United States Patent [19]

Cipolli et al.

[11] Patent Number: 5,210,120
[45] Date of Patent: May 11, 1993

[54] SELF-EXTINGUISHING POLYMERIC COMPOSITIONS COMPRISING OLIGOMERIC 2,4-DIAMINO-6-HYDROXY-1,3,5-TRIAZINES AND PHOSPHATES AND/OR PHOSPHONATES

[75] Inventors: Roberto Cipolli, Novara; Enrico Masarati, Piacenza; Gilberto Nucida, Milan; Roberto Oriani, Milan; Mario Pirozzi, Milan, all of Italy

[73] Assignee: Ministero Dell'Universita' e Della Ricerca Scientifica e Technologica, Rome, Italy

[21] Appl. No.: 785,813

[22] Filed: Oct. 31, 1991

[30] Foreign Application Priority Data

Nov. 2, 1990 [IT] Italy .............................. 21966 A/90

[51] Int. Cl.$^5$ .......................... C08J 5/10; C08K 5/34; C08L 23/00
[52] U.S. Cl. .................................... 524/100; 524/91; 524/96; 524/415; 524/416; 524/101
[58] Field of Search .................... 524/91, 96, 100, 101, 524/415, 416

[56] References Cited

U.S. PATENT DOCUMENTS

| | | | |
|---|---|---|---|
| 3,206,407 | 9/1965 | Lutwack | 252/78 |
| 3,301,797 | 1/1967 | Drucker et al. | 260/2 |
| 4,504,610 | 3/1985 | Fontanelli et al. | 524/96 |
| 4,966,931 | 10/1990 | Akitaya et al. | 524/100 |
| 4,997,876 | 3/1991 | Scarso | 524/706 |
| 5,096,961 | 3/1992 | Eberspach | 524/707 |

FOREIGN PATENT DOCUMENTS 1164865 4/1984 Canada .
0326082 8/1989 European Pat. Off. .

*Primary Examiner*—Paul R. Michl
*Assistant Examiner*—U. K. Rajguru
*Attorney, Agent, or Firm*—Oblon, Spivak, McClelland, Maier & Neustadt

[57] ABSTRACT

Polymeric compositions endowed with high self-extinguishing characteristics to flame, based on thermoplastic polymers or polymers having elastomeric properties, especially olefin polymers and copolymers, comprising:

a) from 89 to 40 parts by weight of a thermoplastic polymer or of a polymer having elastomeric properties;

b) from 8 to 33 parts by weight of one or more phosphates and/or phosphonates of ammonium or of amine;

c) from 3 to 27 parts by weight of one or more oligomeric compounds derived from the 2,4-diamino-6-hydroxy-1,3,5-triazine, having the general formula (I):

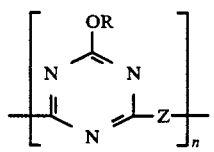

23 Claims, No Drawings

SELF-EXTINGUISHING POLYMERIC COMPOSITIONS COMPRISING OLIGOMERIC 2,4-DIAMINO-6-HYDROXY-1,3,5-TRIAZINES AND PHOSPHATES AND/OR PHOSPHONATES

The present invention relates to self-extinguishing compositions based on thermoplastic polymers or polymers having elastomeric properties, especially olefinic polymers and copolymers, containing particular triazinic compounds combined with phosphates and/or phosphonates of ammonium or of amine.

Several solutions to reduce or remove the combustibility of polymers are known in the art. Some of these solutions are based on the use of metal compounds, especially antimony bismuth or arsenic, combined with organic compounds partially halogenated and thermally unstable, such as chlorinated parafinic waxes.

Other solutions are based on the use of substances able to produce intumescence. The formulations of the intumescent type are generally consisting of the polymer and of at least three main additives: one essentially phosphorated, the purpose of which is to form an impermeable semisolid vitreous layer during the combustion, this layer being essentially consisting of polyphosphoric acid, and to activate the process for the formation of the intumescence; a second containing nitrogen which acts as foaming agent and a third containing carbon which acts as carbon donor to give an insulating cellular carbon layer (char) between the polymer and the flame.

Examples of intumescent formulations of this type are those described in U.S. Pat. No. 3,810,862 (Phillips Petroleum Co.) consisting of melamine, pentaerythritol and ammonium polyphosphate, U.S. Pat. No. 4,727,102 (Vamp s.r.l.) consisting of melamine cyanurate, a hydroxyalkylderivative of the isocyanuric acid and ammonium polyphosphate, and in the published Patent Application WO 85/05626 (Plascoat U.K. Limited) consisting of several phosphorus and nitrogen compounds, among which, in particular, a combination of melamine phosphate, pentaerythritol and ammonium polyphoshate.

In more recent formulations together with the use of a phosphorus organic compound, an organic compound containing nitrogen, generally an aminoplastic resin obtained by condensation of urea, melamine or dicyandiamide with formaldehyde is used.

Examples of formulations based on two additives are those described in U.S. Pat. No. 4,504,610 (Montedison S.P.A.) consisting of oligomeric derivatives of 1,3,5-triazine and ammonium polyphosphate and in European Patent 14 463 (Montedison S.p.A.) consisting of organic compounds selected from benzylguanamine and reaction products between aldehydes and many nitrogenous cyclic compounds, in particular benzylguanamine-formaldehyde copolymers, and of ammonium polyphosphate.

It is also possible to obtain self-extinguishing compositions using monocomponent additives, containing in the organic molecule both nitrogen and phosphorus, as described in U.S. Pat. No. 4,201,705 (Borg-Warner Corp.).

These intumescent retarding systems give to the polymer containing them the property of forming a carbon residue in consequence of a fire or application of a flame. Retarding systems of this type show many advantages: absence of corrosion phenomena in apparatus wherein polymers are worked, lower emission of smoke in comparison with systems containing metal compounds and halogenated hydrocarbons, especially the possibility of giving satisfactory antiflame properties to polymers using a lower quantity of total additive and therefore without an excessive reduction of mechanical properties of polymers themselves.

The Applicant have now found that polymeric compositions showing very good antiflame properties can be obtained by using a class of oligomeric compounds derived from the 2,4-diamino-6-hydroxy-1,3,5-triazine whose effectiveness is higher than that of the products known in the art.

More specifically the compositions of the present invention comprise:

a) from 89 to 40 parts by weight of a thermoplastic polymer or polymer having elastomeric properties;

b) from 8 to 33, preferably from 12 to 30, parts by weight of one or more phosphates and/or phosphonates of ammonium or of amine;

c) from 3 to 27, preferably from 5 to 20, parts by weight of one or more oligomeric compounds derived from the 2,4-diamino-6-hydroxy-1,3,5-triazine, having the general formula (I):

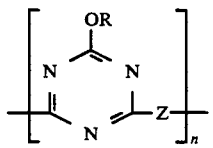

wherein:

R = hydrogen; $-C_mH_{2m}-Y$ wherein
  m is an integer comprised between 1 and 8, preferably between 1 and 4;
  Y is hydrogen; CN; $-O(C_1-C_4)$-alkyl; $-O(C_2-C_4)$-alkenyl; $(C_6-C_{12})$-cycloalkyl or -alkylcycloalkyl; $-O(C_6-C_{12})$-aryl;

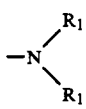

wherein radicals $R_1$, equal or different among them, are $(C_1-C_4)$-alkyl or $(C_3-C_4)$-alkenyl; or the group:

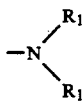

is replaced by a heterocyclic radical bound to the alkyl chain through the nitrogen atom, and containing another heteroatom, preferably selected among O, S, N; $(C_2-C_6)$-alkenyl; $(C_6-C_{12})$-cycloalkyl or -alkylcycloalkyl; $(C_6-C_{12})$-aryl or -aralkyl;

n = integer comprised between 2 and 50;

Z is a divalent or polyvalent radical comprised in one of the following formulae:

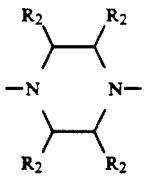

wherein radicals $R_2$, equal or different among them, are hydrogen or $(C_1-C_4)$-alkyl;

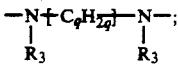 (III)

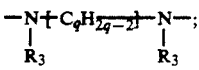 (IV)

wherein q is an integer comprised between 2 and 14; $R_3$ is hydrogen; $(C_1-C_4)$-alkyl; $(C_2-C_6)$-alkenyl; $(C_1-C_4)$-hydroxyalkyl;

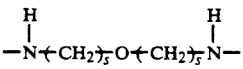 (V)

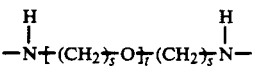 (VI)

wherein s is an integer comprised between 2 and 5 and t is an integer comprised between 1 and 3;

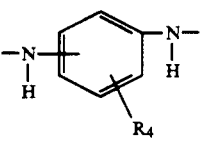 (VII)

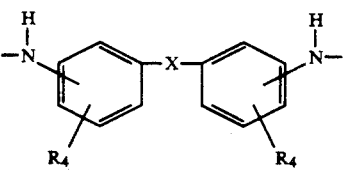 (VIII)

wherein:

X is a direct bond C—C; O; S; S—S; SO; $SO_2$; NH; $NHSO_2$; NHCO; N=N; $CH_2$;

$R_4$ is hydrogen; hydroxyl; $(C_1-C_4)$-akyl; $(C_1-C_4)$-alkoxy;

 (IX)

wherein A can be a saturated or unsaturated cycle;

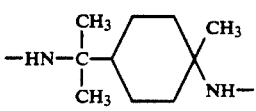 (X)

$$-HN+CH_2\!\!\to_{s}\!\!N\diagup\!\!\diagdown N+CH_2\!\!\to_{s}\!\!NH- \quad (XI)$$

wherein s has the previously defined meaning;

$$-N\!\!-\!\!\left[(CH_2)_{\overline{s}}N\!-\!\right]_p\!(CH_2)_{\overline{s}}N\!-\!\atop{R_5}\quad\quad\quad\quad\atop{R_5} \quad (XII)$$

wherein:

$R_5$ hydrogen or $(C_1-C_4)$-alkyl;

p is an integer comprised between 1 and 5;

indexes s, equal or different among them, have the previously defined meaning;

$$-N\!\!-\!\!\left[(CH_2)_{\overline{r}}N\!-\!\atop{(CH_2)_{\overline{r}}N\!-\!\atop{R_5}}\right]_v\!(CH_2)_{\overline{r}}N\!-\!\atop{R_5}$$

wherein:

$R_5$ has the previously defined meaning;

r is an integer comprised between 2 and 4;

v is 1 or 2.

The above mentioned compounds of general formula (I), are particularly stable to heat and therefore they maintain a high activity as flame retarders also after hot working processes of the polymeric compositions containing them.

Furthermore, the compositions object of the present invention have the advantage to give rise, in the event of a fire, to a very reduced and not darkening emission of smoke Examples of radical R in the general formula (I) are: methyl; ethyl; propyl; isopropyl; n-butyl; isobutyl; ter-butyl; n-pentyl; isopentyl; n-hexyl; ter-hexyl; octyl; ter-octyl; ethenyl; propenyl; butenyl; isobutenyl; hexenyl; cyclohexyl; propylcyclohexyl; butylcyclohexyl; phenyl; benzyl; 2-phenylethyl; cyanomethyl; 2-cyanoethyl; 2-methoxyethyl; 2-methoxypropyl; 3-methoxypropyl; 4-methoxybutyl; 5-methoxypentyl; 6-methoxyhexyl; 7-methoxyheptyl; 7-methoxyoctyl; 2-ethoxyethyl; 3-ethoxypropyl; 4-ethoxybutyl; 5-ethoxypentyl; 3-propoxypropyl; 3-butoxypropyl; 4-butoxybutyl; 4-isobutoxybutyl; 5-propoxypentyl; 2-cyclohexyloxyethyl; 2-ethenyloxyethyl; 2-phenoxyethyl; 2-(N,N-dimethylamino)ethyl; 3-(N,N-dimethylamino)propyl; 4-(N,N-dimethylamino)butyl; 5-(N,N-dimethylamino)pentyl; 4-(N,N-diethylamino)butyl; 5-(N,N-diethylamino)pentyl; 5-(N,N-diisopropylamino)pentyl; 4-(N,N-dipropylamino)butyl; 2-(N,N-diisopropylamino)ethyl; 2-(N-methyl-N-1-propenylamino)ethyl; 2-(N,N-di-1-propenylamino)ethyl; 4-(N,N-di-1-propenylamino)butyl; etc.

Examples of heterocyclic radicals which may replace the group:

are: pyrrolidine, piperidine, morpholine, thiomorpholine, piperazine, 4-methylpiperazine; 4-ethylpiperazine; etc.

Examples of radicals —Z— are those which are formed by removal of a hydrogen atom from each reacted amino group, from the following compounds: piperazine; 2-methylpiperazine; 2,5-dimethylpiperazine; 2,3,5,6-tetramethylpiperazine; 2-ethylpiperazine; 2,5-diethylpiperazine; 1,2-diaminoethane; 1,3-diaminopropane; 1,4-diaminobutane; 1,5-diaminopentane; 1,6-diaminohexane; 1,8-diaminooctane; 1,10-diaminodecane; 1,12-diaminododecane; N,N'-dimethyl-1,2-diaminoethane; N-methyl-1,3-diaminopropane; N-ethyl-1,2-diaminoethane; N-isopropyl-1,2-diaminoethane; N-(2-hydroxyethyl)-1,2-diaminoethane; N,N'-bis(2-hydroxyethyl)-1,2-diaminoethane; N-(2-hydroxyethyl)-1,3-diaminopropane; N-hexenyl-1,6-diaminohexane; N,N'-diethyl-1,4-diamino-2-butene; 2,5-diamino-3-hexene; 2-aminoethylether; (2-aminoethoxy)-methylether; 1,2-bis(2-aminoethoxyethane; 1,3-diaminobenzene; 1,4-diaminobenzene; 2,4-diaminotoluene; 2,4-diaminoanisol; 2,4-diaminophenol; 4-aminophenylether; 4,4'-methylenedianiline; 4,4'-diaminobenzanilide; 3-aminophenylsulfone; 4-aminophenylsulfone; 4-aminophenyldisulfide; 4-aminophenylsulfoxide; 1,3-bis-(aminomethyl)benzene; 1,4-bis(aminomethyl)benzene; 1,3-bis(aminomethyl)cyclohexane; 1,8-diamino-p-menthane 1,4-bis(2-aminoethyl)piperazine; 1,4-bis(3-aminopropyl)piperazine; 1,4-bis-(4-aminobutyl)piperazine; 1,4-bis-(5-aminopenthyl)piperazine; bis(2-aminoethyl)amine; bis(3-aminopropyl)amine; bis(4-aminobutyl)amine; bis(5-aminopentyl)amine; bis[2-(N-methylamino)ethyl]amine; 2-N-butylbis(2-aminoethyl)amine; bis[3-(N-methylamino)propyl]amine; N-(3-aminopropyl)-1,4-diaminobutane; N-(3-aminopropyl)-1,5-diaminopentane; N-(4-aminobutyl)-1,5-diaminopentane; tris(2-aminoethyl)amine; tris(3-aminopropil)amine; tris(4-aminobutyl)amine; tris[2-(N-ethylamino)ethyl]amine; N,N'-bis(2-aminoethyl)-1,2-diaminoethane; N,N'-bis(3-aminopropyl)-1,3-diaminopropane; N,N'-bis(2-aminoethyl)-1,3-diaminopropane; N,N'-bis (3-aminopropyl)-1,2-diaminoethane; N,N'-bis(3-aminopropyl)-1,4-diaminobutane; bis[2-(2-aminoethyl)aminoethyl]amine; N,N'-bis[2-(2-aminoethyl)aminoethyl]-1,2-diaminoethane; N,N'-bis[3-(2-aminoethyl)aminopropyl]-1,2-diaminoethane; N,N,N',N'-tetrakis(2-aminoethyl)-1,2-diaminoethane; etc.

Particularly preferred are the compounds of general formula (I) wherein R is hydrogen or wherein R is substituted by the group:

$$-(C_mH_{2m})-Y$$

wherein m is an integer comprised between 1 and 4 and Y is hydrogen.

Oligomeric compounds comprised in the general formula (I) not mentioned in the examples, but equally advantageously useable in the self-extinguishing polimeric compositions object of the present invention are those reported in Table 1.

TABLE 1

| Compounds | R | —Z— | n |
|---|---|---|---|
| 1 | —CH$_3$ | —HNCH$_2$CH$_2$OCH$_2$CH$_2$NH— | 18 |
| 2 | —CH$_2$CH$_2$N(CH$_3$)$_2$ | —N⌐⌐N— (piperazine) | 15 |
| 3 | H | —HNCH$_2$—⟨cyclohexane⟩—CH$_2$NH— | 17 |
| 4 | —C$_2$H$_5$ | —HNCH$_2$CH$_2$CH$_2$NH— | 20 |
| 5 | H | N(CH$_2$CH$_2$NH—)$_3$ | 20 |
| 6 | H | —HNCH$_2$CH$_2$NCH$_2$CH$_2$NCH$_2$CH$_2$NH— | 12 |
| 7 | —CH$_3$ | —HN(CH$_2$)$_3$—N(H)—(CH$_2$)$_3$NH— | 15 |
| 8 | —CH$_2$—⟨phenyl⟩ | —N⌐⌐N— (piperazine) | 16 |
| 9 | —CH$_2$CH$_2$CN | —HN—CH$_2$CH$_2$—N(CH$_2$CH$_2$OH)— | 16 |
| 10 | —CH$_2$CH$_2$OCH=CH$_2$ | —HN—CH$_2$CH$_2$—N—CH$_2$CH$_2$—NH— | 16 |

TABLE 1-continued

| Compounds | R | —Z— | n |
|---|---|---|---|
| 11 | H | —N(CH₃)—CH₂CH₂—N(CH₃)— | 20 |
| 12 | —CH₂CH₂O—C₆H₅ | —N(piperazine)N— | 17 |
| 13 | —CH₂CH₂OCH₃ | —N(piperazine)N— | 18 |
| 14 | —CH₂CH₂—C₆H₁₁ | —HN—CH₂CH₂—NH—CH₂CH₂—NH— | 12 |
| 15 | —CH₂CH₂N(pyrrolidine) | —N(2-methylpiperazine)N— | 13 |
| 16 | —CH₂CH₂O—C₆H₁₁ | —N(piperazine)N— | 15 |
| 17 | H | —N(C₂H₅)—CH₂—CH=CH—CH₂—N(C₂H₅)— | 12 |
| 18 | H | —HN—C₆H₄—COHN—C₆H₄—NH— | 10 |
| 19 | —CH₂—CH=CH₂ | —N(CH₂CH₂OH)—CH₂CH₂—N(CH₂CH₂OH)— | 12 |
| 20 | —CH₂CH₂N(morpholine) | —HN—CH₂CH₂—NH— | 18 |

When R is different from hydrogen the compounds of general formula (I) can be prepared by allowing a halide of the cyanuric acid, for example the chloride, to react with a reagent of the general formula (XIV):

R—OH          (XIV)

wherein R has the previously defined meaning, at temperatures comprised between 10° and 110° C. in a suitable solvent (such as for instance acetone, methylene chloride, toluene, xylene, etc;) or in an excess of the reagent itself if it is able to act as solvent (such as for instance methyl alcohol, ethyl alcohol, etc.) in the presence of an acid acceptor (such as for instance NaOH, NaHCO₃, Na₂CO₃, triethylamine, collidine, etc.) thus obtaining the intermediate of the general formula (XV):

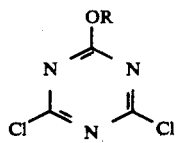
(XV)

This intermediate, either separated or not, is allowed to react under conditions analogous to the preceding ones, but working at temperatures comprised between 0° and 150° C. and therefore with solvents which are also compatible with the mentioned temperatures (such as for instance, acetonitrile, water, xylene, orthodichlorobenzene, etc.) with a polyamine of the general formula (XVI):

H—Z—H          (XVI)

wherein Z is a radical comprised in one of the general formulae from (II) to (XIII), in the presence of an acidity acceptor.

The molar ratio between the intermediate (XV) and the polyamine (XVI) varies from 1:1 to obtain linear oligomers up to a maximum of 3.5:1 to obtain cross-linked oligomers.

An alternative method consists in allowing a halide of the cyanuric acid, for instance the chloride, to react with a polyamine of the general formula (XVI), defined as above, in the suitable molar ratio, always under conditions analogous to those previously described, at temperatures comprised between 0° and 60° C., to give the intermediate of the general formula (XVII):

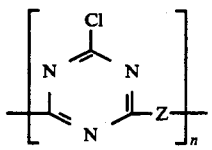

(XVII)

wherein Z and n have the previously defined meaning.

From this intermediate, either separated or not, the compounds of the general formula (I) are obtained according to the following procedure:
a) when R is hydrogen, by hydrolysis reaction either with an acid (such as for instance hydrochloric acid, hydrobromic acid, sulfuric acid, phosphoric acid, etc.) at temperatures comprised between 60° and 100° C., or with a base (such as for instance sodium hydroxide, potassium hydroxide, etc.) at temperatures comprised between 100° and 180° C.;
b) when R is different from hydrogen, by condensation reaction with a reagent of the general formula (XIV), as above defined, in a suitable solvent (such as for instance, toluene, xylene, orthodichlorobenzene, etc.) or in an excess of the reagent (XIV) if it is able to act as solvent (such as for instance methyl alcohol, ethyl alcohol, etc.) in the presence of a base (such as for instance sodium hydroxide, potassium hydroxide, metal sodium, etc.) at temperatures comprised between 60° and 150° C.

From the compounds of the general formula (I), wherein R is different from hydrogen, preferably a($C_1$-$C_4$)-alkyl, it is possible to obtain the corresponding compounds wherein R is hydrogen by hydrolysis reaction, either with an acid, working at temperatures comprised between 80° and 140° C. or with a base, working at temperatures comprised between 100° and 180° C., using the same reagents indicated for the hydrolysis of intermediates of general formula (XVII).

Among the phosphates there are preferred ammonium polyphosphates which are comprised in the general formula $(NH_4)_{n+2}P_nO_{3n+1}$ wherein n represents an integer equal to or higher than 2; preferably the molecular weight of polyphosphate has to be sufficiently high to warrant a lower solubility in water. As example, n varies preferably from 2 to 500.

The composition of polyphosphates having the above indicated formula, wherein n is a number sufficiently high and preferably comprised between 5 and 500, practically is the one which corresponds to the formula of methaphosphates $(NH_4PO_3)_n$.

An example of these polyphosphates is that known by the trade name "Exolit 422" (manufactured and sold by Hoechst Co.) and having the composition $(NH_4PO_3)_n$ wherein n is higher than 50; another example is the product known under the trademark "Phos-Chek P/30" (Monsanto Chemical) and having analogous composition.

Another polyphosphate which can be advantageously used, in particular owing to its reduced solubility in water, is that known under the trade name "Exolit 462" (manufactured and sold by Hoechst) and corresponding to Exolit 422 microen capsulated in melamine-formaldehyde resin.

Other phosphates useable are those deriving from amines, such as for instance dimethylammonium or diethylammonium phosphate, ethylenediamine phosphate, ortho or pyrophosphate of melamine.

Among phosphonates very good results have been obtained using ammonium phosphonates (mono or poly substituted) derived from mono and polyphosphonic acids, examples of which are: ethane-1,1,2-triphosphonic acid; 2-hydroxyethane-1,1,2-triphosphonic acid; propane-1,2,3-triphosphonic acid; methylphosphonic acid; ethylphosphonic acid; n-propylphosphonic acid; n-butylphosphonic acid; phenylphosphonic acid; 1-aminoethane-1,1-diphosphonic acid; 1-hydroxyethane-1,1-diphosphonic acid; 1-hydroxydodecane-1,1-diphosphonic acid; phosphonoacetic acid; 2-phosphonopropionic acid; 3-phosphonopropionic acid; 2-phosphonobutyric acid; 4-phosphonobutyric acid; amino-tris(methylenphosphonoic) acid; ethylenediaminotetra(-methylenephosphonic) acid; hexamethylenediaminotetra(methylenephosphonic) acid; diethylenetriaminopenta(methylenephosphonic) acid; etc.

Among polymers useable in compositions of the present invention polymers and copolymers of olefins of the general formula $R-CH=CH_2$ wherein R is a hydrogen atom or a ($C_1$-$C_8$)-alkyl or -aryl radical, are preferred; in particular:
1. isotactic or prevailingly isotactic polypropylene;
2. HDPE, LLDPE, LDPE polyethylene;
3. crystalline copolymers of propylene with minor amounts of ethylene and/or other alpha-olefins, such as for instance butene-1, hexene-1, octene-1; 4-methyl-pentene-b 1;
4. heterophasic compositions comprising: (A) a homopolyeric fraction of propylene, or one of copolymers described at point (3) and (B) a copolymeric fraction consisting of elastomeric copolymers of ethylene with an alpha-olefin, optionally containing minor amounts of a diene, wherein the alpha-olefin is preferably selected from propylene and butene-1;
5. elastomeric copolymers of ethylene with alpha-olefins optionally containing minor amounts of a diene. Examples of dienes among those more commonly present in the above mentioned elastomeric copolymers are butenediane, ethylidene-norbornene, hexadiene 1,4.

Among the polymers of olefins of the formula $R-CH=CH_2$ wherein R is an aryl radical polystyrene "crystal" and anti-shock are preferred.

Other examples of polymers commonly useable are acrylonitrile/butadiene/styrene (ABS) copolymers and styrene/acrylonitrile (SAN) copolymers; polyurethane (polyester and polyether); polyethyleneterephthalate; polybutyleneterephthalate; polyamides, etc.

The self-extinguishing compositions of the present invention can be prepared according to known methods: for instance, the phosphate and/or phosphonate of ammonium or of amine is firstly intimately mixed with one or more nitrogenous compounds of the general formula (I) finely milled (preferably with particles lower than 70 microns) and the mixture thus obtained is added to the polymer in a turbomixer to form a homogeneous blend which is estruded and granulated. The granular product thus obtained can be transformed into many articles according to anyone of the known molding techniques. The first retardant additives of the present invention are able to be used also in the field of the flame retardant paints.

The examples reported hereinafter illustrate the features of the invention without limiting them.

EXAMPLE 1

Into a 2 liters reactor, equipped with stirrer, thermometer, feeding funnel, condenser and cooling bath, 600 cc of methyl alcohol, 80 cc of water and 100.8 g of sodium bicarbonate are introduced.

The mixture is cooled to 10° C. and 110.7 g of cyanuric acid chloride are fed. The temperature is allowed to rise up to 30° C. and is kept at this value for about 1 hour, until the carbon dioxide release is completed.

The exothermy itself is sufficient to maintain the desired temperature.

The whole is cooled to 5° C. and successively 700 cc of cold water are added.

The product formed is filtered off and washed on the filter with cold water,

By drying the cake in oven under vacuum at 60° C., 92.1 g of the intermediate (XVIII):

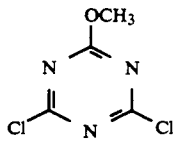

(XVIII)

is obtained in the form of a white crystalline powder having a melting point (m.p.) 90°-92° C. and chlorine content equal to 39.27% (theoretic: 39.44%).

Furthermore, the structure of the intermediate (XVIII) has been confirmed by NMR analysis.

In the same 2 liters reactor, but equipped with heating bath, 400 cc of acetonitrile and 72.0 g of the intermediate (XVIII) are introduced.

The solution is cooled to 5° C. and a solution consisting of 24.0 g of ethylenediamine in 100 cc of acetonitrile is fed within about 1 hour.

Thereafter the temperature is raised to 70° C. and a solution consisting of 84.8 g of sodium carbonate in 250 cc of water is fed within 3 hours.

The mixture is heated to boiling and is kept under reflux for about 3 hours.

Then the distillation of acetonitrile starts, while keeping the volume unchanged by addition of water.

The whole is cooled to 50° C. and the product formed is filtered and washed on the filter with water at 50° C.

By drying the cake in oven at 100° C., 66.2 g of the product:

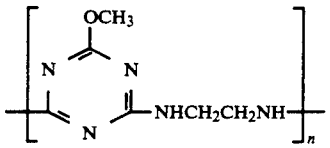

are obtained in form of white crystalline powder having m.p. higher than 300° C. and n=25.

EXAMPLE 2

Into a 0.5 liter reactor equipped as in example 1, 200 cc of water, 78.8 g of a 37% by weight hydrochloric acid solution and 66.8 g of the product obtained in example 1 are introduced.

The mass is heated to boiling and is maintained under reflux for about 16 hours.

At the end the mass is cooled to 50° C. and is neutralized by adding a solution consisting of 32 g of sodium hydroxide in 100 cc of water. The whole is kept under stirring for further 30 minutes, thereafter the product formed is filtered and washed on the filter with water at 50° C.

By drying the cake in oven at 100° C., 56.9 g of the product:

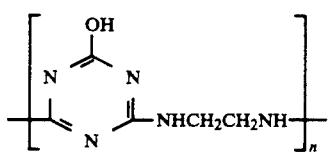

is obtained in the form of a white crystalline powder having a m.p. higher than 300° C. and n=25.

EXAMPLE 3

In a 2 liters reactor equipped as in example 1 there are introduced, 800 cc of xylene, 50 cc of water and 90.0 g of the intermediate (XVIII) and then under stirring within about 20 minutes, 43.0 of piperazine.

The temperature of the dispersion rises up to 35°-40° C.; by means of the outer bath the dispersion is kept at 40° C. and is maintained under agitation for about 1 hour.

Thereafter, 20.0 g of sodium hydroxide dissolved in 40 cc of water are added within 2 hours and at 40° C.

Subsequently the temperature is raised to 80° C. and is maintained under agitation at this value for about 1 hour.

Further 20.0 g of sodium hydroxide dissolved in 40 cc of water are then added within 2 hours.

The temperature is gradually raised up to 120°-125° C. while removing the water azeotropically.

The temperature is kept at this value for about 2 hours, then the whole is cooled to room temperature and the product formed is filtered.

The cake is well squeezed and then is washed abundantly with water.

After drying in oven at 100° C., 91.8 g of the product:

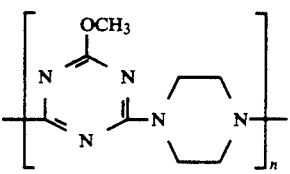

is obtained in the form of a white crystalline powder, having m.p. higher than 300° C. and n=20.

EXAMPLE 4

In a 1 liter reactor equipped as in example 1, 400 cc of acetone, 92.2 g of cyanuric acid chloride and 53.3 g of n-butyl alcohol are introduced.

The mixture is cooled to 0° C. and within about 1 hour 60.5 g of collidine are fed while keeping the temperature within the range of from 0° to 5° C.

The whole is kept under agitation at 5° C. for further 1 hour and then the temperature is allowed to raise up to the room temperature.

After agitation for further two hours, the collidine hydrochloride is removed by filtration.

The acetonic solution is then poured on 500 cc of cold water and treated with 3 portions of 200 cc each of ethyl ether.

Ether extracts are collected, then the distillation is carried out by separating at first the ethyl ether and thereafter collecting at 148°-150° C., 80.4 g of the intermediate

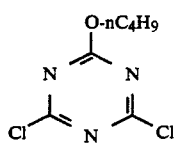

(XIX)

in form of a colorless liquid having a chlorine content equal to 31.67% (theoretic: 31.98%) and the structure of which is further confirmed by NMR analysis.

In the same 1 liter reactor, but equipped with a heating bath, 400 cc of orthodichlorobenzene, 30 cc of water, 55.5 g of the intermediate (XIX) and under agitation 21.5 g of piperazine are introduced.

The temperature of the dispersion raises up to 40°-45° C.

By working as described in example 3, 55.3 g of the product;

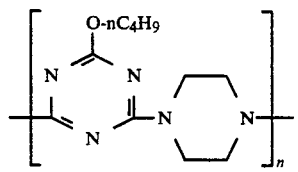

is obtained in the form of a white crystalline powder having a m.p. higher than 300° C. and n=17.

EXAMPLE 5

In a 2 liters reactor, equipped as in example 1, 400 cc of acetone and 100 g of cyanuric acid chloride are introduced.

The suspension is cooled to 0°-5° C. and within 1 hour 23.4 g of piperazine are added.

Always at 0°-5° C. and within 2 hours 23.3 g of piperazine and 10.8 g of sodium hydroxide dissolved in 50 cc of water are contemporarily fed in such a manner to maintain the pH at about 3.

The temperature is raised to 20° C. and within about two hours 10.8 g of sodium hydroxide dissolved in 50 cc of water are fed in such a manner to maintain the pH at about 5.

The temperature is gradually raised from 20° to 60° C. by feeding within about 2 hours a solution consisting of 21.8 g of sodium hydroxide in 100 cc of water.

The whole is kept under agitation at 60° C. for further 2 hours and then is cooled to room temperature and the product formed is filtered and washed with water on the filter.

By drying the cake in oven at 100° C. 104.9 g of the intermediate (XX):

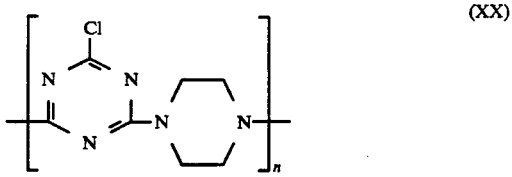

is obtained in the form of a white crystalline powder having m.p. higher than 300° C., chlorine content equal to 17.70% (theoretic: 17.94%) and n=15.

The structure of the intermediate (XX) has been further confirmed by IR spectroscopic analysis.

In a 1 liter reactor, equipped with stirrer, thermometer, feeding funnel, reflux condenser and heating bath, 450 cc of water, 98.7 g of the intermediate (XX) and 98.6 g of a 37% by weight solution of hydrochloric acid are introduced.

The mixture is heated to 80° C. and is maintained under stirring at this temperature for 2 hours; thereafter it is heated to boiling point and kept under reflux for about 6 hours.

Thereafter 60 g of sodium hydroxide dissolved in 150 cc of water are added.

The mixture is allowed to cool to 50° C. and the product formed is filtered and washed with water at 50° C. on the filter.

By drying the cake in oven at 100° C., 88.8 g of the product:

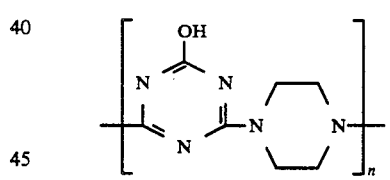

is obtained in the form of a white crystalline powder, having m.p. higher than 300° C. and n=15.

EXAMPLE 6

In a 2 liters reactor equipped as in example 1, 200 cc of acetonitrile, 200 cc of water and 41.2 g of diethylenetriamine are introduced.

The solution is cooled to 0° C. and keeping the temperature from 0° to 3° C., a solution consisting of 72 g of the intermediate (XVIII) in 500 cc of acetonitrile is fed within about 1 hour.

The mixture is then heated to 70° C. and at this temperature 84.8 g of sodium carbonate in 250° C. of water are fed within 3 hours.

The whole is heated to boiling and is maintained under reflux for 2 hours.

Thereafter, the distillation of acetonitrile is started, while the dispersion is allowed to reach the boiling temperature of water.

The dispersion is kept under reflux for further 2 hours and thereafter it is cooled to room temperature.

The product formed is filtered and washed on the filter with water.

By drying the cake, 76.6 g of the product:

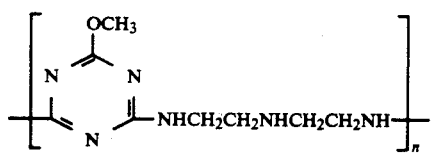

is obtained in the form of a white crystalline powder having m.p. higher than 300° C. and n=12.

EXAMPLES 7-15

By working under conditions analogous to those described in examples from 1 to 6 the products of the general formula (I) listed in Table 2 are prepared, all these products having m.p. higher than 300° C.

MOORE plate press, by working for 7 minutes under a pressure of 40 kg/cm².

On the thus obtained little plates the self-extinguishing level has been determined measuring the oxygen index (L.O.I. according to ASTM D-2863/77) in a Stanton Redcroft apparatus, and applying the "Vertical Burning Test" which allows to classify the material at three levels 94 V-0, 94 V-1 and 94 V-2 according to UL 94 standards (edited by "Underwriters Laboratories'-'—USA).

In Table 3 values obtained using an isotatic polypropylene in flakes having Melt Flow Index equal to 12 and a fraction insoluble in boiling n-heptane equal to 96% by weight are reported.

In Table 4 there are reported values obtained using a low density polyethylene in granules having Melt Flow Index equal to 7; a polystyrene in granules containing 5% by weight of butadiene rubber and having Melt Flow Index equal to 9; a thermoplastic polyurethane

TABLE 2

| Example No. | R | —Z— | n |
|---|---|---|---|
| 7 | H | —HN—⌬—NH— (para-phenylene) | 20 |
| 8 | H | —HN—(CH₂)₆—NH— | 22 |
| 9 | cyclohexyl | —N(piperazine)N— | 18 |
| 10 | H | —HNC(CH₃)₂—⌬—C(CH₃)(NH)— | 15 |
| 11 | H | —HNCH₂CH₂—N—CH₂CH₂NH— (N unsubstituted) | 16 |
| 12 | phenyl | —N(piperazine)N— | 17 |
| 13 | H | —HN—CH₂CH₂—N(H)—CH₂CH₂—NH— | 20 |
| 14 | H | —HN(CH₂)₃—N(piperazine)N—(CH₂)₃NH— | 14 |
| 15 | H | —HNCH₂CH₂N(CH₂CH₂OH)— | 18 |

TABLES 3 AND 4

Tests reported in these tables relate to polymeric compositions containing products of the general formula (I) prepared according to the preceding examples. Specimens have been produced in form of little plates having a thickness of about 3 mm by molding mixtures of the granulated polymers together with additives in a either polyester (ESTANE 54600 ® by Goodrich) or polyether (ESTANE 58300 ® by Goodrich) in granules having specific gravity equal to 1.19 and 1.10 g/cm³ respectively; an ethylene-propylene elastomeric copolymer having a propylene percentage content by weigh equal to 45; an acrylonitrile-butadiene-styrene terpolymer having specific gravity equal to 1.06 g/cm³, Melt Flow Index equal to 1.6 containing about 40% of acrylonitrile and styrene and 20% of butadiene.

TABLE 3

| Example N. | Product Ex. N. | Product | PP (1) | AO (2) | APP (1) | L.O.I. (ASTM D2863) | UL 94 3 mm |
|---|---|---|---|---|---|---|---|
| 16 | 1 | 6.0 | 75 | 1 | 18.0 | 34.5 | V0 |
| 17 | 2 | 6.0 | 75 | 1 | 18.0 | 36.5 | V0 |
| 18 | 3 | 12.0 | 75 | 1 | 12.0 | 31.4 | V0 |
| 19 | 3 | 4.6 | 75 | 1 | 19.4 | 35.5 | V0 |
| 20 | 4 | 6.3 | 74 | 1 | 18.7 | 35.0 | V0 |
| 21 | 5 | 6.0 | 75 | 1 | 18.0 | 34.7 | V0 |
| 22 | 6 | 6.0 | 75 | 1 | 18.0 | 37.0 | V0 |
| 23 | 7 | 6.8 | 72 | 1 | 20.2 | 31.8 | V1 |
| 24 | 8 | 6.0 | 72 | 1 | 21.0 | 32.4 | V0 |
| 25 | 9 | 6.4 | 73 | 1 | 19.6 | 33.2 | V1 |
| 26 | 10 | 7.0 | 71 | 1 | 21.0 | 32.9 | V0 |
| 27 | 11 | 6.0 | 75 | 1 | 18.0 | 35.9 | V0 |
| 28 | 12 | 6.2 | 74 | 1 | 18.8 | 30.8 | V1 |
| 29 | 13 | 6.0 | 75 | 1 | 18.0 | 36.5 | V0 |
| 30 | 14 | 6.8 | 75 | 1 | 17.2 | 33.2 | V0 |
| 31 | 15 | 6.8 | 75 | 1 | 17.2 | 35.8 | V0 |
| 32 | 3 | 6.4 | 76 | 1 | 16.6(*) | 34.0 | V0 |
| 33 | 13 | 6.8 | 75 | 1 | 17.2(*) | 36.3 | V0 |
| 34 | 3 | 6.2 | 73 | 1 | 19.8(3) | 32.8 | V0 |
| 35 | 6 | 7.8 | 72 | 1 | 19.2(4) | 34.4 | V0 |

(1)PP = polypropylene
APP = ammonium polyphosphate Exolit 422 ® (Hoechst)
(*)APP microincapsulated with melamine-formaldehyde resin Exolit 462 ® (Hoechst)
(2)AO = antioxidant
Mixture consisting of 2 parts of dilaurylthiopropionate and 1 part of tetra[3-(3,5-di-terbutyl-4-hydroxyphenyl)propionate] of pentaerythritol
(3)monoammonium salt from 1-aminoethane-1,1-diphosphonic acid
(4)monoammonium salt from 1-hydroxyethane-1,1-diphosphonic acid.

TABLE 4

| Example No | Polymeric supp.(2) | Product EX. No. | Product | Polymer | AO(3) | APP(1) | L.O.I. (ASTM-D2863) | UL 94 3 mm |
|---|---|---|---|---|---|---|---|---|
| 36 | LDPE | 1 | 9.7 | 65 | 1 | 24.3 | 32.5 | V0 |
| 37 |  | 3 | 7.2 | 70 | 1 | 21.8 | 31.5 | V0 |
| 38 |  | 5 | 7.3 | 70 | 1 | 21.7 | 35.2 | V0 |
| 39 |  | 13 | 8.5 | 65 | 1 | 25.5 | 33.8 | V0 |
| 40 | HIPS | 5 | 9.7 | 60 | 1 | 29.3 | 33.6 | V0 |
| 41 | PU estere | 2 | 7.2 | 70 | 1 | 21.8 | 36.8 | V0 |
| 42 |  | 5 | 7.2 | 70 | 1 | 21.8 | 39.0 | V0 |
| 43 |  | 6 | 7.2 | 70 | 1 | 21.8 | 38.0 | V0 |
| 44 | PU etere | 2 | 6.8 | 70 | 1 | 22.2 | 34.3 | V0 |
| 45 | PP/PE | 3 | 8.3 | 70 | 1 | 20.7 | 35.0 | V0 |
| 46 |  | 6 | 7.3 | 70 | 1 | 21.7 | 33.8 | V0 |
| 47 | ABS | 15 | 9.2 | 60 | 1 | 29.8 | 33.2 | V0 |

(1)APP = ammonium polyphosphate
(2)LDPE = low density polyethylene
HIPS = Polystyrene containing 5% of butadiene rubber
PU (ester) = polyurethane polyester
PU (ether) = polyurethane polyether
PP/PE = propylene-ethylene copolymer
ABS = acrylonitrile-butadiene-styrene terpolymer
(3)AO = antioxidant
Mixture consisting of 2 parts of dilaurylthiopropionate and 1 part of tetra[3-(3,5-di-terbutyl-4-hydroxyphenyl)propionate] of pentaerythritol.

We claim:
1. Self-extinguishing polymeric compositions comprising:
a) from 89 to 40 parts by weight of a thermoplastic polymer or of a polymer having elastomeric properties;
b) from 8 to 33 parts by weight of one or more phosphates and/or phosphonates of ammonium or of amine;
c) from 3 to 27 parts by weight of one or more oligomeric compounds derived from 2,4-diamino-6-hydroxy-1,3,5-triazine, having the general formula (I):

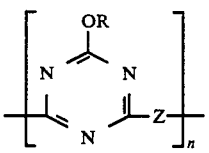

wherein:
R = hydrogen; —$C_mH_{2m}$—Y wherein
m is an integer comprised from 1 and 8;
Y is hydrogen; CN; —O($C_1$-$C_4$)-alkyl; —O($C_2$-$C_4$)-alkenyl; ($C_6$-$C_{12}$)-cycloalkyl or -alkylcycloalkyl; —O($C_6$-$C_{12}$)-aryl;

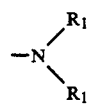

wherein radicals $R_1$, equal or different among them, are ($C_1$-$C_4$)-alkyl or ($C_3$-$C_4$)-alkenyl; or the group:

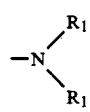

is replaced by a heterocyclic radical bound to the alkyl chain through the nitrogen atom, and optionally containing another heteroatom; ($C_2$-$C_6$)-alkenyl; ($C_6$-$C_{12}$)-cycloalkyl or -alkyl-cycloalkyl;
n = integer comprised between 2 and 50;
Z is a bivalent or polyvalent radical comprised in one of the following formulae:

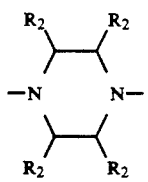 (II)

wherein radicals $R_2$, equal or different among them, are hydrogen or ($C_1$-$C_4$)-alkyl;

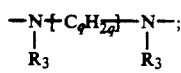 (III)

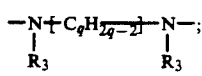 (IV)

wherein q is an integer comprised between 2 and 14; $R_3$ is hydrogen; ($C_1$-$C_4$)-alkyl; ($C_2$-$C_6$)-alkenyl; ($C_1$-$C_4$)-hydroxyalkyl;

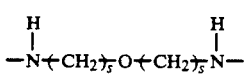 (V)

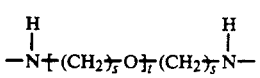 (VI)

wherein s is an integer comprised between 2 and 5 and t is an integer comprised between 1 and 3;

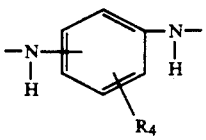 (VII)

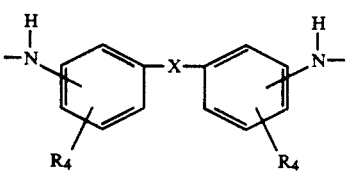 (VIII)

wherein
X is a direct bond C—C; O; S; S—S; SO; $SO_2$; NH; $NHSO_2$; NHCO; N=N; $CH_2$;
$R_4$ is hydrogen; hydroxyl; ($C_1$-$C_4$)-alkyl; ($C_1$-$C_4$)-alkoxy;

 (IX)

wherein A can be a saturated or unsaturated cycle;

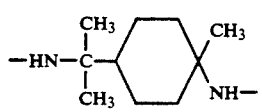 (X)

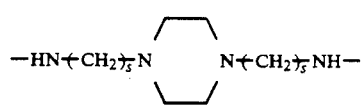 (XI)

wherein s has the previously defined meaning;

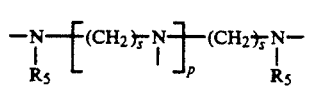 (XII)

wherein:
$R_5$ is hydrogen or ($C_1$-$C_4$)-alkyl;
p is an integer comprised between 1 and 5;
indexes s, equal or different among them, have the previously defined meaning;

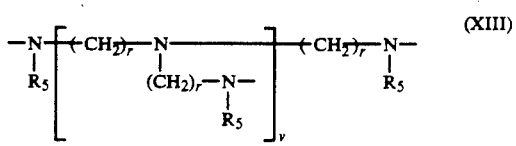 (XIII)

wherein:
$R_5$ has the previously defined meaning;
r is an integer comprised between 2 and 4;
v is 1 or 2.

2. Self-extinguishing polymeric compositions, according to claim 1, wherein R in the general formula (I) is hydrogen.

3. Self-extinguishing polymeric compositions, according to claim 1, wherein R in the general formula (I) is substituted by a group:

$$-C_mH_{2m}-Y$$

wherein m is an integer comprised between 1 and 4 and Y is hydrogen.

4. Self-extinguishing polymeric compositions, according to claim 1, wherein the group:

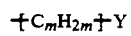

is replaced by a heterocyclic radical selected from: pyrrolidine; piperidine; morpholine; thiomorpholine; piperazine; 4-methylpiperazine; 4-ethylpiperazine.

5. Self-extinguishing polymeric compositions, according to any one of claims from 1 to 4, wherein the ammonium phosphate or phosphates (b) have the general formula $(NH_4)_{n+2}P_nO_{3n+1}$ wherein n is an integer equal to or higher than 2.

6. Self-extinguishing polymeric compositions, according to any one of claims from 1 to 4 wherein the ammonium phosphate or phosphates (b) have the general formula $(NH_4PO_3)_n$ wherein n is an integer comprised between 50 and 500.

7. Self-extinguishing polymeric compositions, according to any one of claims from 1 to 4 wherein the amine phosphate or phosphates (b) are selected from dimethylammonium or diethylammonium phosphate; ethylenediamine phosphate; ortho or pyrophosphate of melamine.

8. Self-extinguishing polymeric compositions, according to any one of claims from 1 to 4 wherein the ammonium phosphonate or phosphonates (b) are those mono or polysubstituted and selected from the salts derived from mono and polyphosphonic acids.

9. Self-extinguishing polymeric compositions, according to any one of claims from 1 to 4, wherein the polymer (a) is selected from polymers and copolymers of olefins of general formula $R-CH=CH_2$ wherein R is a hydrogen atom or a $(C_1-C_8)$-alkyl or -aryl radical; acrylonitrile/butadiene/styrene (ABS) copolymers; styrene/acrylonitrile (SAN) copolymers; polyurethane; polyethyleneterephthalate; polybutyleneterephthalate; polyamides.

10. Self-extinguishing polymeric compositions, according to claim 9 wherein polymers and copolymers of olefins are selected from:
1) isotactic or prevailingly isotactic polypropylene;
2) HDPE, LLDPE, LDPE polyethylene;
3) crystalline copolymers of propylene with minor amounts of ethylene and/or other alpha-olefins;
4) heterophasic compositions comprising (A) a homopolymeric fraction of propylene or one of copolymers mentioned at point (3) and (B) a copolymeric fraction formed by elastomeric copolymers of ethylene with an alpha-olefin, containing optionally minor proportions of a diene, wherein the alpha-olefin is selected from propylene and butene-1; and
5) elastomeric copolymers of ethylene with alpha-olefins containing optionally minor proportions of a diene.

11. Manufactured molded articles obtained from the compositions of any one of claims 1 to 4.

12. Self-extinguishing compositions according to any one of claims 1-4, wherein Z is of the formula (II).

13. Self-extinguishing compositions according to any one of claims 1-4, wherein Z is of the formula (III).

14. Self-extinguishing compositions according to any one of claims 1-4, wherein Z is of the formula (IV).

15. Self-extinguishing compositions according to any one of claims 1-4, wherein Z is of the formula (V).

16. Self-extinguishing compositions according to any one of claims 1-4, wherein Z is of the formula (VI).

17. Self-extinguishing compositions according to any one of claims 1-4, wherein Z is of the formula (VII).

18. Self-extinguishing compositions according to any one of claims 1-4, wherein Z is of the formula (VIII).

19. Self-extinguishing compositions according to any one of claims 1-4, wherein Z is of the formula (IX).

20. Self-extinguishing compositions according to any one of claims 1-4, wherein Z is of the formula (X).

21. Self-extinguishing compositions according to any one of claims 1-4, wherein Z is of the formula (XI).

22. Self-extinguishing compositions according to any one of claims 1-4, wherein Z is of the formula (XII).

23. Self-extinguishing compositions according to any one of claims 1-4, wherein Z is of the formula (XIII).

* * * * *